016 United States Patent [19]
Pickart

[11] Patent Number: 4,810,693
[45] Date of Patent: * Mar. 7, 1989

[54] METHOD FOR INDUCING BIOLOGICAL COVERINGS IN WOUNDS

[75] Inventor: Loren R. Pickart, Bellevue, Wash.

[73] Assignee: ProCyte Corporation, Redmond, Wash.

[*] Notice: The portion of the term of this patent subsequent to Feb. 28, 2006 has been disclaimed.

[21] Appl. No.: 49,646

[22] Filed: May 11, 1987

Related U.S. Application Data

[63] Continuation-in-part of Ser. No. 699,824, Feb. 8, 1985, Pat. No. 4,665,054.

[51] Int. Cl.$^4$ ............................................. A61K 37/02
[52] U.S. Cl. ..................................................... 514/18
[58] Field of Search ........................................... 514/18

[56] References Cited

U.S. PATENT DOCUMENTS 4,665,054  5/1987  Pickart ................................. 514/18

Primary Examiner—Delbert R. Phillips
Attorney, Agent, or Firm—Seed and Berry

[57] ABSTRACT

Methods are disclosed for (a) enhancing the formation of a natural biological dressing composed primarily of serum proteins; (b) enhancing the reestablishment for free, full-thickness skin grafts in warm-blooded animals; (c) enhancing the establishment of split-thickness skin grafts; and (d) increasing the rate of wound closure in warm-blooded animals. The methods utilize GHL-Cu or a derivative thereof.

31 Claims, 5 Drawing Sheets

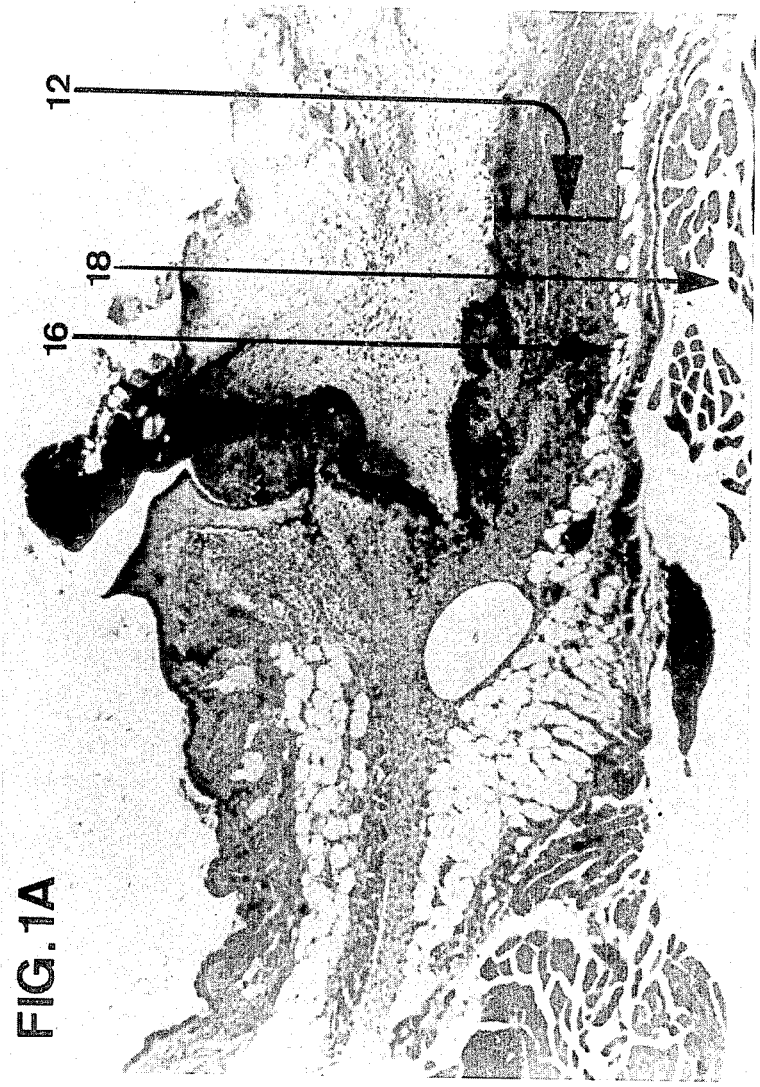

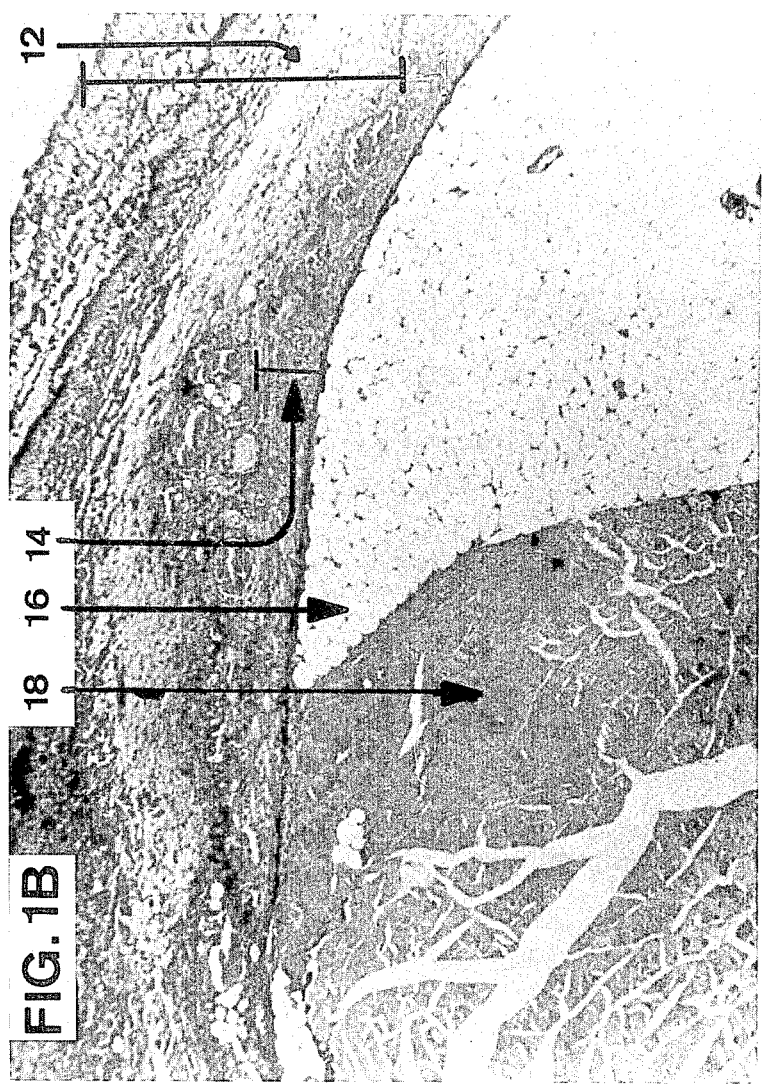

FIG. 2A
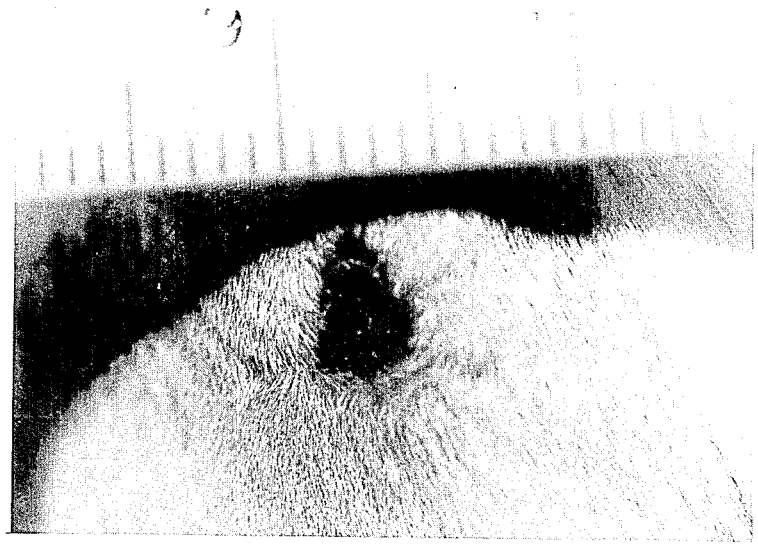
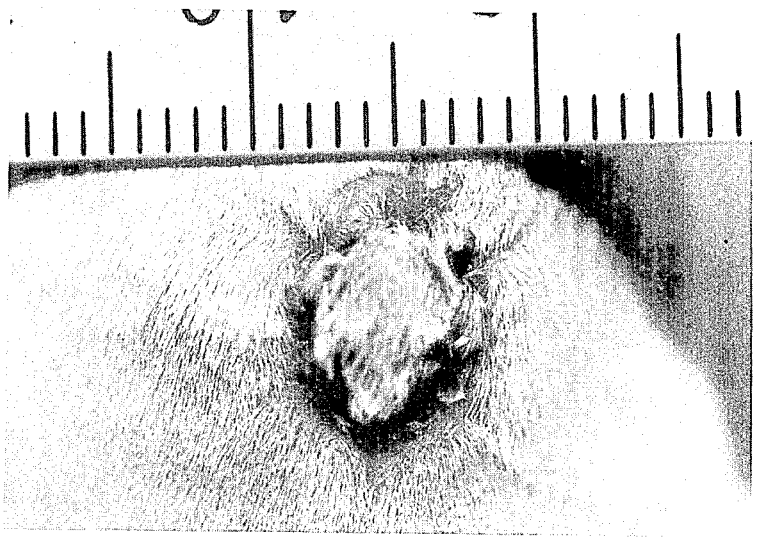
FIG. 2B

METHOD FOR INDUCING BIOLOGICAL COVERINGS IN WOUNDS

CROSS-REFERENCE TO RELATED APPLICATION

This application is a continuation-in-part of U.S. Ser. No. 699,824 filed Feb. 8, 1985, which application issued as U.S. Pat. No. 4,665,054 on May, 12, 1987.

DESCRIPTION

1. Technical Field

The present invention relates to wound-healing compositions in general, and more specifically, to the use of glycyl-L-histidyl-L-lysine:copper(II) (GHL-Cu) and derivatives thereof within a method for enhancing the biological coverings associated with wounds.

2. Background Art

Mechanisms of wound-healing tissue repair in humans and other mammals are often inadequate and incomplete. Delayed healing markedly increases hospitalization costs, and often the wound continues as a chronic sore that requires extensive attention and medical care in order to control infection and tissue necrosis. Even when such wounds finally heal, the "wound area" is often devoid of the ability to respond to tactile stimulus, and is often filled with excessive deposits of collagen that lead to permanent scarring. The need for improved wound-healing compositions also extends to wounds generated by surgical procedures. For instance, although cosmetic surgery is one of the fastest growing medical specialty areas, the success of such procedures is limited by the adequacy of healing in the typically adult and elderly clientele. Further, hair transplants often fail due to an inadequate blood supply around the transplant. Enhanced healing and neovascularization of the transplant would enhance the establishment of the graft.

The rapidity of reestablishment of a biological coverage on wound surfaces is a critical element in the healing prognosis. Natural open wounds are first covered by a blood and plasma exudate which dries to form the initial "scab" that covers the wound. This scabby layer forms a short-term protective coverage from outside elements while healing proceeds under this layer.

For longer-term coverage of extensive wounds, surgeons often resort to transplants in which a thin piece of superficial skin (called a "split-thickness skin graft") is implanted over the wound to form island of skin cells that can overgrow the surface. Deeper skin wounds often require a more extensive skin transplant (called a "full-thickness skin flap") in which the entire skin down to the muscular layers is moved to cover wound. Split-thickness flaps are hampered by the low degree of surgical "take." Typically, only about 20% to 40% of the transplanted skin successfully reestablish itself in its new position. Full-thickness flaps are even more difficult to reestablish in a new site. Surgeons are usually constrained to leave one end of the flap attached to a blood supply, while the other end is stretched to the new site to be sewn in place. Only after the transplanted end of the flap reestablishes a new blood supply is the other end of the flap moved to the new site to complete the transplant. Such procedures often result in extensive loss of tissue and additional pain and suffering for the patient.

DISCLOSURE OF THE INVENTION

Briefly stated, this invention discloses a method for enhancing the formation of a natural biological dressing composed primarily of serum proteins. The method generally comprises administering to a wound a therapeutically effective amount of a composition comprising either glycyl-L-histidyl-L-lysine:copper(II) or a composition comprising a derivative of GHL-Cu having the general formula:

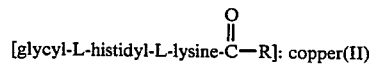

wherein R is selected from the group consisting of alkyl moieties containing from 1 to 18 carbon atoms, aryl moieties containing from 6 to 12 carbon atoms, alkoxy moieties containing from 1 to 12 carbom atoms, and aryloxy moieties containing from 6 to 12 carbon atoms, or where R is L-prolyl-L-valyl-L-phenylalanyl-L-valine or L-valyl-L-phenylalanyl-L-valine.

In another aspect of the present invention, a method for enhancing the reestablishment of free, full-thickness skin grafts in warm-blooded animals is disclosed. The method generally comprises administering the skin graft a composition comprising a derivative of GHL-Cu having the general formula:

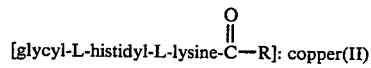

wherein R is selected from the group consisting of alkyl moieties containing from 1 to 18 carbon atoms and aryl moieties containing from 6 to 12 carbon atoms, or where R is L-prolyl-L-valyl-L-phenylalanyl-L-valine or L-valyl-L-phenylalanyl-L-valine.

Within a third aspect of the present invention, a method for enhancing the establishment of split-thickness skin grafts in warm-blooded animals is disclosed. This method generally comprises administering to the skin graft either a composition comprising glycyl-L-histidyl-L-lysine:copper(II) or a composition comprising a derivative of GHL-Cu having the general formula:

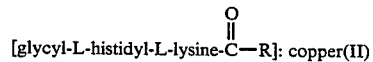

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

Within yet another aspect of the present invention, a method for increasing the rate of wound closure in warm-blooded animals is disclosed. The method generally comprises administering to the wound an effective amount of a composition comprising GHL-Cu or a derivative thereof as set forth above.

The derivatives of the present invention are described in detail in pending U.S. patent application Ser. Nos. 699,824 and 040,460, which applications are hereby incorporated by reference.

In addition, within all of the methods described above, the composition may comprise a derivative of GHL-Cu having the general formula:

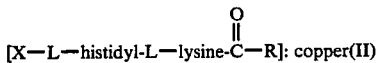

[X—L—histidyl-L—lysine-C—R]: copper(II)

wherein X is glycyl-L-alanyl, glyclyl-L-seryl or glyclyl-L-valyl, and wherein R is selected from the group consisting of alkyl moieties containing from 1 to 18 carbon atoms and aryl moieties containing from 6 to 12 carbon atoms, or where R is L-prolyl-L-valyl-L-phenylalanyl-L-valine or L-valyl-L-phenylalanyl-L-valine.

When the compositions are infiltrated or injected with physiological saline as described herein, a suitable concentration includes from about 0.1 to 5 mg of GHL-Cu or a derivative thereof per milliliter of vehicle.

Other aspects of the present invention will become evident upon reference to the followed detailed description and attached drawings.

BRIEF DESCRIPTION OF THE DRAWINGS

FIG. 1A is a photograph of a biological covering over a surgical wound.

FIG. 1B is a photograph of a biological covering over a surgical wound treated with a representative composition of the present invention.

FIGS. 2A and 2B are photographs of full-thickness skin grafts;

FIG. 2A is a control (where the skin graft did not establish), and

FIG. 2B is a skin graft treated with a representative composition of the present invention.

FIG. 3A is a control and

FIG. 3B is a skin graft treated with a representative composition of the present invention.

BEST MODE FOR CARRYING OUT THE INVENTION

Figure 3A:
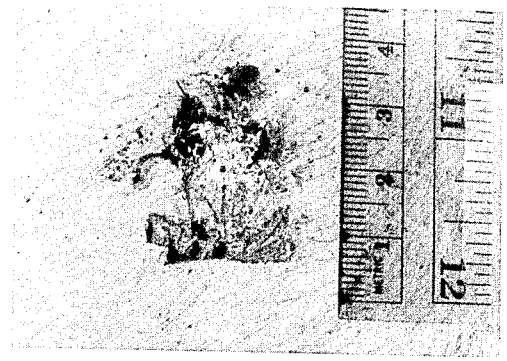
FIGS. 3A and 3B are photographs illustrating the establishment of split-thickness skin grafts in warm-blooded animals.

The use of GHL-Cu and derivatives thereof described herein is useful in (a) the establishment of a thicker biological covering over wounds; (b) the reestablishment of free, full-thickness skin flaps; (c) the establishment of split-thickness skin grafts; and (d) increasing the rate of wound closure.

GHL-Cu and the derivatives described herein may also be used in combination with other factors reported to improve other facets of healing. In this manner, a synergistic effect may be obtained that provides a clinical efficacy better than that obtained with any single factor. Further, while the compositions described herein stimulate a spectrum of healing process, clinical wounds often vary considerably in their properties and healing patterns, leading one to utilize a combination of a composition described herein and another factor. For example, nerve regeneration is defective in many burns, and therefore one might add a specific nerve growth factor to GHL-Cu or a derivative thereof to enhance nerve regrowth into the burn area.

Examples of factors with other reported healing properties include epidermal growth factor, fibroblast growth factor, nerve growth factor, transforming growth factors α and β, any of a number of angiogenic growth factors, haparin, fibronectin, fibrin, platelet-derived growth factor, enzymatic superoxide dismutase, extracts of blood or factors from the blood, and other similar factors. In addition, GHL-Cu and derivatives thereof could also be used to aid the in vivo establishment of biological cultures of skin cells.

Within the present invention, one may utilize a ratio of GHL or a derivative to copper of 1:1 or 2:1. However, within a preferred embodiment, optimal healing occurs with a ratio of 0.50:0.75 copper atoms per GHL molecule. Copper in molar excess to GHL (>1.00) is loosely bound and may delay healing since it is believed that free copper salts attract inflammatory cells such as neutrophils.

In wounds treated with GHL-Cu and derivatives thereof, there is a greater liquid (serum-like) exudate over the wounds. The treated wounds have a "wetter" appearance, and the scabby layer that forms over the wound is substantially thicker. This phenomenon occurs after localized injection, and also when high concentrations are topically applied to a newly created surgical defect. In theory, one could imagine that such a phenomenon could complicate the healing of burn wounds by increasing eschar formation over the wound. However, within the present invention, some of the best results have been observed on the recovery of burned (100° C.) tissue. This is probably due in large part to the fact that the GHL-Cu and derivatives thereof induce attraction of macrophages which aid in removal of burn eschar despite the increased exudate over the burn area. In addition, since white cell migration into the wound is delayed in burned tissue, an adequate influx of white cells may be more critial in burn healing than the amount of exudate.

As noted above, the present invention is useful in establishing a thicker biological covering over wounds. The first covering over a fresh wound is a thin covering formed from the blood and serum that dry over the wound. Since it often takes several days before a thick biological covering forms over a wound or an abrasion, the present invention is valuable in protecting the wound from infection and further blood loss, through the generation of a thicker biological covering.

Use of the present invention to enhance the production of a thick productive scab through topical application may be useful in healing horses with barbed wire cuts, where the wounds are very common and the thin skin of the horses makes stitching very difficult. In humans, application of these compounds to an open, "abrasion-type" wound produces a thicker, more protective scab over the wound.

In addition, the present invention is also useful in the reestablishment of free, full-thickness skin flaps in warm-blooded animals. Full-thickness skin flaps are necessary in many reconstructive surgical procedures. Because of the difficulty in moving full-thickness flaps of skin, the common procedure is to leave one end of the skin flap attached to a supply of blood while the other end of the flap is sewn to the body area to be covered. Only after the moved section of the flamp has established a new blood flow can the other end of the flap be moved to a new position. These cumbersome procedures are surgically difficult, and portions of the transplanted skin flaps often die before new blood vessels can adequately nourish the transplanted skin flap.

The present invention substantially increases the efficiency of skin flap transplantations, and therefore has significant practical value.

Similarly, the present invention is useful in the establishment of split-thickness skin grafts. Such grafts are used to transfer skin pieces from one part of a patient's body to an area where the skin has been damaged by a burn, abrasion, or other injury. However, usually only a small portion of the transplanted skin is established in the new area. The present invention substantially increases the quantity of established skin in this type of transplant procedure.

The effectiveness of the compositions described herein in the transplantation of split-thickness skin grafts and full-thickness skin flaps also makes these compositions of value in the transplantation of other types of organs, such as kidneys and hearts. Other compounds with superoxide dismutase activity, such as proteinacious superoxide dismutase, a protein of a molecular weight of 32,000, have been used to improve the transplantation of skin flaps, hearts, kidneys, and other organs. Proteinacious superoxide dismutase acts to improve transplant "take" by protecting the tissue from an ischemia/re-perfusion injury after the reestablishment of blood flow into the tissues. Briefly stated, when hypoxic tissues reestablish normal blood flow, they overproduce superoxide anion ("toxic oxygen"), and compounds with superoxide dismutase activity can detoxify this toxic oxygen before it causes cellular damage. These results further suggest that GHL-Cu and derivatives thereof would also protect against milder types of tissue damage due to ischemia/re-perfusion injuries, such as those which occur after myocardial infarctions, soft tissue injuries, acute spinal cord injuries, and impairments of blood flow to other organs of the body.

In addition to the derivatives described above, other chemical modifications could be made to alter the biological activity of the derivatives of the present invention. For instance, glycine may be replaced by a variety of other small amino acids, including alanine, serine and valine. Further, the copper(II) binding affinity of the molecule could be increased by addition of an N-terminal amino acid, such as glycine, to convert glycyl-L-histidyl-L-lysine to glycyl-L-glycyl-L-histidyl-L-lysine. In addition, glycine could be added to a derivative as described above to create the corresponding tetrapeptide. The binding affinity for copper(II) of the imadazole group in the histidyl residue could be modified by substitution of 3-methylhistidine for histidine or by extending the lysyl side chains by adding additional carbon atoms to the chain.

To summarize the examples that follow, Example 1 illustrates the synthesis of glycyl-L-histidyl-L-lysine benzyl ester:copper(II). Example 2 demonstrates the synthesis of glycyl-L-histidyl-L-lysine n-octyl ester:copper(II). Example 3 illustrates (A) the synthesis of glycyl-L-hystidyl-L-lysine n-stearyl ester:copper(II), and (B) its synthesis by an alternataive procedure. Based upon either procedure, one skilled in the art could substitute n-palmityl alcohol (16 carbons) for the n-stearyl alcohol (18 carbons) to yield glycyl-L-histidyl-L-lysine n-stearyl ester:copper(II). Example 4 illustrates the synthesis of glycyl-L-histidyl-L-lysyl-L-prolyl-L-valyl-L-phenylalanyl-L-valine:copper(II) and glycyl-L-histidyl-L-lysyl-L-valyl-L-phenylalanyl-L-valine:copper(II). Example 5 demonstrates the establishment of a thicker biological covering over a wound. Example 6 demonstrates the reestablishment of free, full-thickness skin grafts. Example 7 demonstrates the reestablishment of split-thickness skin grafts. Example 8 demonstrates a method for increasing the rate of wound closure in a warm-blooded animal.

The following examples are offered by way of illustration and not by way of limitation.

EXAMPLES

Preparation of GHL-Cu for Use in Animals

GHL was purified by dissolving in glass distilled water (50 mg/ml), then centrifuging at 20,000×g for 1 hour at 3° C. This removes poorly water-soluble material remaining from the synthesic procedure. The supernatent is lyophilized, then passed through a Sephadex G-10 column at 3° C. in a solvent of 0.5% acetic acid. The main peak that elutes behind the solvent front (monitored by absorption at 254 nanometers) is lyophilized to dryness. GHL-Cu was prepared by combining purified GHL with equimolar amounts of cupric acetate and sodium hydroxide, then precipitated by use of ethanol addition and low temperature by published methods (Perkins et al., *Inorg. Chim. Acta* 67: 93–99, 1984).

Sources of chemicals

Chemicals and peptide intermediates utilized in the following examples may be purchased from the following suppliers: Sigma Chemical Co. (St. Louis, Mo.); Peninsula Laboratories (San Carlos, Calif.); Aldridge Chemical Co. (Milwaukee, Wis.); Vega Biochemicals (Tucson, Ariz.); Pierce Chemical Co. (Rockford, Ill.); Research Biochemiicals (Cleveland, Ohio); Van Waters and Rogers (South San Fransisco, Calif.); Bachem, Inc. (Torrence, Calif.).

EXAMPLE 1

Synthesis of glycyl-L-histidyl-L-lysine benzyl ester:copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzoylcarbonyl-L-lysine benzyl ester, was coupled to t-butyloxycarbonylglycine with dicyclohexylcarbodiimide as a coupling agent. Blocking groups were removed by catalytic hydrogenation using 10% palladium on carbon in glacial acetic acid. After lyophilization, the product, glycil-L-histidyl-L-lysine benzyl ester, was dissolved in water and purified by ion-exchange chromatography on Dowex 50×-4 cation-exchange resin and elution with 0.1M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine benzyl ester:copper(II).

EXAMPLE 2

Synthesis of glycyl-L-histidyl-L-lysine n-octyl ester:copper(II)

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anhydrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-L-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycyl-$N^{im}$-benzyloxycarbonyl-L-histidyl-$N^e$-benzyloxycarbonyl-L-lysinate. This was dissolved in glacial acetic acid and hydrogenated overnight.

The resultant n-octyl ester of glycyl-L-histidyl-L-lysine was converted to the copper-complex by the addition of an equimolar quantity of copper diacetate. The pH was raised to neutrality with sodium hydroxide. The solution was centrifuged at 20,000 g for 1 hour at 3° C. to remove poorly water-soluble material. The supernatant was lyophilized to obtain glycyl-L-histidyl-L-lysine n-octyl ester:copper(II).

EXAMPLE 3

A. Synthesis of glycyl-L-histidyl-L-lysine n-stearyl ester:copper(II)

A mixture of $N^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl $N^e$-benzyloxycarbonyl-L-lysinate. The product was dissolved in tetrahydrofuran and mixed with $N^a$-t-butyloxycarbonyl-$N^{im}$-benzoyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-stearyl $N^{im}$-benzyloxycarbonyl-L-histidyl-$N^e$-benzyloxycarbonyl-L-lysinate, which was dissolved in tetrahydrofuran, isobutyl chloroformate, N-methylmorpholine and benzyloxycarbonylglycine to form n-stearyl benzyloxycarbonylglycyl-$N^{im}$-benzyloxycarbonyl-L-histidyl-$N^e$-benzyloxycarbonyl-L-lysinate. The product was dissolved in 50% trifluoroacetic acid in dichloromethane for 30 minutes, then evaporated, forming n-stearyl ester glycyl-L-histidyl-L-lysine.

The resultant molecule, glycyl-L-histiyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ester:copper(II)

$N(\epsilon)$-benzyloxycarbonyl-L-lysine, n-stearyl alcohol, p-toluenesulfonic acid monohydrate, and benzene are refluxed together using a Dean-Stark trap to azeotropically remove the evolved water. After cooling to room temperature and then adding dry ethyl ether, n-stearyl $N(\epsilon)$-benzyloxycarbonyl-L-lysinate p-toluenesulfonate salt is collected by filtration, treated with 2M aqueous potassium bicarbonate solution, and extracted into dichloromethane. Evaporation gives free amine, which is redissolved in dry tetrahydrofuran (THF) and added to a stirring solution of $N(\alpha)$-t-butyloxycarbonyl-$N(im)$-benzyloxycarbonyl-L-histidine, N-methylmorpholine, and isobutyl chloroformate in dry THF at $-15°$ C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine and isobutyl chloroformate in dry THF at $-15°$ C. The formed, fully protected tripeptide ester is totally deblocked by treatment with hydrogen gas in glacial acetic adid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper-complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

EXAMPLE 4

Synthesis of glycyl-L-histidyl-L-lysyl-L-prolyl-L-valyl-L-phenylalanyl-L-valine:copper(II) and of glycyl-L-histidyl-L-lysyl-L-valyl-L-phenylalanyl-L-valine:copper(II)

These peptides are synthesized by standard solid-phase methods common to the peptide field (J. Stewart and J. Joung, *Solid Phase Peptide Synthesis*, Pierce Chemical Co., 1984). Briefly stated, Boc-Val-O-Resin was sequentially coupled with other blocked amino acids using dicyclohexylcarbodiimide as a reaction agent. Protected amino acids, resins for solid-phase synthesis, and coupling agents were obtained from Peninsula Laboratories, San Carlos, Calif. Blocked amino acids are added in sequentianl order to obtain the desired peptide. The final peptide is deblocked using hydrogen fluoride. The final peptide is dissolved in 0.5% acetic acid and purified by passage through a Sephadex G-15 column (Pharmacia). Addition of equimolar cupric acetate, followed by lyophilization, produces the active molecule.

EXAMPLE 5

Establishment of a Thicker Biological Covering over Wounds

Wounds in mice were induced by removal of a 1.5 cm diameter circular patch of skin from the back. CHL-Cu and derivatives thereof were swabbed onto the fresh wound. As shown in FIG. 1A (control), there is only a thin biological covering 12, with new skin 14 not yet apparent. Further, the fat cells 16 near the muscle 18 have not been fully replaced. However, as shown in FIG. 1B, application of GHL-Cu and derivatives thereof markedly increased the amount of serum-like exudate over the wound and the thickness of the biological covering 12 over the wound. Referring again to FIG. 1B, the compositions induced the presence of thicker new skin 14 and more fat cells 16. The most effective concentrations were in the range of 4 to 20 milligrams of GHL-Cu or a derivative thereof per milliliter of water or physiological saline.

EXAMPLE 6

Reestablishment of Free, Full-Thickness Skin Flaps

Although free, full-thickness skin grafts are also very difficult to establish without extensive necrosis, the derivatives of the present invention markedly improved viability, and the "take" rate of such grafts is described in more detail hereinafter.

Mice were anestetized with pentobarbital, shaved, and a 1.5 cm by 1.5 cm circle marked on the center of the back. The circular patch of full-thickness skin was carefully removed from the animal and then sewn back with 4 equidistant stitches. 30 μg of GHL-Cu or a derivative thereof was infiltrated into the center of the free flap after surgery and at 24 hours.

Control flaps (FIG. 2A) rapidly hardened and fell off in 4 to 6 days, while the treated flaps (FIG. 2B) stayed in place, established themselves and grew hair. In the flaps that recovered, the recovery was histologically apparent by 12 days, but still proceeded at a slow rate. In some flaps, the entire flap recovered, while in others only a significant portion of the flap area recovered. It will be evident to one skilled in the art that two treatment may not be necessary in this regard. Infiltration of from 5–30 $\mu g/cm^2$ of surface area is suitable for use herein.

The results of histological staining and pathological analysis of the reestablished mouse flaps showed that the flaps were well vascularized, with no evidence of necrosis. By 12 days after surgery, the flaps showed a normal healing process associated with injured skin, characterized by the presence of granulation tissue and with little fibrous scarring. The skin flap, aside from the reactive process, resembles adjacent native tissue and is well adhered to the native tissue. Included among the elements showing viability were skeletal muscles in deep portions, viable epidermis and viable skin appendages. In the area between the graft and the native tissue, there was a continuous necrotic debris with extensive infiltrates representing material normally found on healing skin. Little collagen or scabbing was observed except in a limited number of edge areas of the flap.

EXAMPLE 7

Split-Thickness Skin Grafts

Figure 3B:
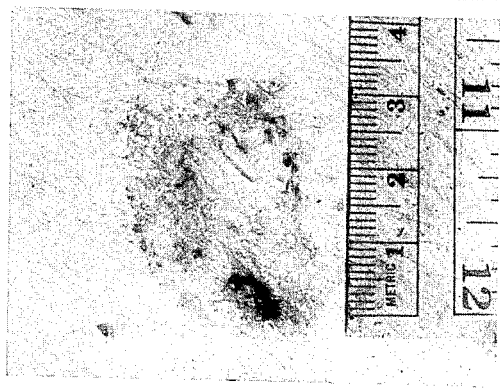

Split-thickness skin graft "take" is improved when GHL-Cu is incorporated into liposomes and applied one time after grafting. In Yorkshire pigs, skin and underlying fat were removed from a 2.5 centimeter square in order to create a wound. A split-thickness skin graft was prepared from another portion of the animal and sewn over the wound area. GHL-Cu was formulated into lipsome vesicles by standard procedures using phophatidyl choline/cholate in a molar ratio of 0.625. The GHL-Cu-containing liposomes (0.1 milliliter liposomes containing 50 micrograms GHL-Cu) were infiltrated into the tissue under the graft, while control grafts (FIG. 3A) received liposomes without GHL-Cu. At 15 days post-grafting, the skin graft group treated with GHL-Cu-containing liposomes (FIG. 3B) had smoothly covered the wound area and blended smoothly into the adjacent skin. In contrast, without GHL-Cu, only the center of the attached skin graft was established and the edges of the wound-margin were still covered with scar tissue. The average area of newly established skin was 1.2 (±0.3) square centimeters in the control animals against 4.3 (±0.7) in the GHL-Cu-treated animals (p value of difference <0.001).

EXAMPLE 8

Acceleration of Wound Closure

This example employs the removal of a circular patch of skin from the back of a mouse, with healing measured by the rate of re-epithelialization and closure of the wound.

Quantification of the effect of GHL-Cu and derivatives thereof on the rate of wound healing of the surgical incision is by the reduction in both the perimeter of the wound and the reduction in the unhealed wound area, along with the preparation of representative histological tissue samples. The rate of wound closure and re-epithelialization is a relatively simple and direct assay of healing and is dependent on the adequacy of the reestablishment of the blood supply and the nutrient flow to the damaged tissue.

The experiment described herein used Swiss-Webster mice (25 gm). At day 0 of the experiment, each mouse was treated with interperitoneal barbiturate, sufficient to provide a deep and long-lasting anesthesia in order to create the wound. A round plate (1.5 cm diameter) was used to mark the boundaries of the skin to be removed from the upper surface of the back immediately behind the forelimbs. The skin and subcutaneous tissue inside the marked circle was sharply incised, down to the lumbo dorsal fascia, and the skin inside the circle removed to produce the area of open wound.

Figure 4:
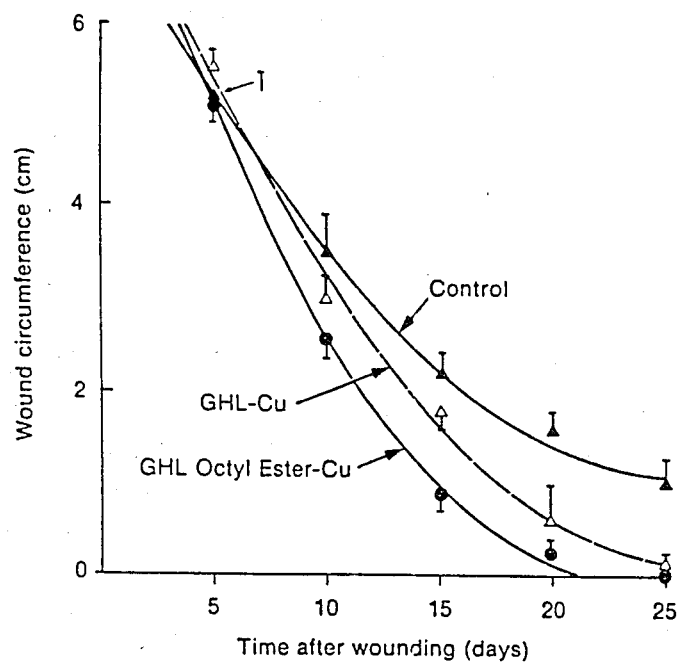
FIG. 4 is a graph illustrating the effect of representative compositions of the present invention upon the rate of wound closure.

In one group of mice, the margins of skin surrounding the circular wound were infiltrated with intradermal infiltration of GHL-Cu or a derivative thereof in 0.03 ml buffered saline. The control mice received the buffered saline only. Every five days for twenty-five days, the wound was debrided to a sharp wound margin and photographed with a scale bar. The circumference and area of each wound were measured with a computerized digitizer, and the results are shown in FIG. 4.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A method for enhancing the formation of a natural biological dressing composed primarily of serum proteins, comprising:
administering to a wound therapeutically effective amount of a composition containing glycyl-L-histidyl-L-lysine:copper(II).

2. The method of claim 1 wherein said composition includes a penetrating agent.

3. The method of claim 1 wherein said composition is admixed with a pharmaceutically acceptable vehicle prior to being administered.

4. A method for enhancing the formation of a natural biological dressing composed primarily of serum proteins, comprising:
administering to a wound a therapeutically effective amount of a composition comprising a derivative of GHL-Cu having the general formula:

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 atoms, or where R is L-prolyl-L-valyl-L-phenylalanyl-L-valine or L-valyl-L-phenylalanyl-L-valine.

5. The method of claim 4 wherein said composition includes a penetrating agent.

6. The method of claim 4 wherein said composition is admixed with a pharmaceutically acceptable vehicle prior to being administered.

7. A method for enhancing the reestablishment of free, full-thickness skin flaps in warm-blooded animals, comprising:
administering to the skin flap an effective amount of a composition comprising glycyl-L-histidyl-L-lysine:copper(II).

8. A method for enhancing the reestablishment of free, full-thickness skin flaps in warm-blooded animals, comprising:
administering to the skin flap an effective amount of a composition comprising a derivative of GHL-Cu having the general formula:

wherein R is selected from the group consisting of alkyl moieties containing from 1 to 18 carbon atoms and aryl moieties containing from 6 to 12 carbon atoms, or where R is L-prolyl-L-valyl-L-phenylalanyl-L-valine or L-valyl-L-phenylalanyl-L-valine.

9. The method of calim 8 wherein said derivative is injected intradermally.

10. The method of claim 8 wherein the alkyl moiety is an unbranched chain.

11. The method of claim 10 wherein the unbranched chain is an N-octyl moiety.

12. The method of claim 8 wherein the alkyl moiety is an N-stearyl moiety.

13. The method of claim 8 wherein the aryl moiety is a benzyl moiety.

14. A method for enhancing the establishment of split-thickness skin grafts in warm-blooded animals, comprising:
administering to the skin graft an effective amount of a composition comprising glycyl-L-histidyl-L-lysine:copper(II).

15. The method of claim 14 wherein said composition is admixed with a pharmaceutically acceptable vehicle prior to being administered to the skin graft.

16. The method of claim 14 wherein said composition is applied topically to said skin graft.

17. A method for enhancing the establishment of split-thickness skin grafts in warm-blooded animals, comprising:
administering to the skin graft a composition comprising a derivative of GHL-Cu having the general formula:

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

18. The method of claim 17 wherein said composition is admixed with a pharmaceutically acceptable vehicle prior to being administereed to said skin graft.

19. The method of claim 17 wherein said composition is applied topically to said skin graft.

20. A method for increasing the rate of wound closure in warm-blooded animals, comprising:
administering to the animal an effective amount of a composition comprising glycyl-L-histidyl-L-lysine:copper(II).

21. The method of claim 20 wherein said composition is admixed with a pharmaceutcially acceptable vehicle prior to administration.

22. The method of claim 20 wherein said composition is injected intradermally.

23. The method of claim 20 wherein said composition is applied topically to the wound.

24. A method for increasing the rate of wound closure in warm-blooded animals, comprising:

administering to the animal an effective amount of a composition comprising a derivative of GHL-Cu having the general formula:

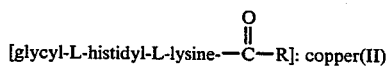

wherein R is selected from the group consisting of alkyl moieties containing from 1 to 18 carbon atoms, aryl moieties containing from 6 to 12 carbon atoms, alkoxy moieties containing from 6 to 12 carbon atoms, or where R is L-prolyl-L-valyl-L-phenylalanyl-L-valine or L-valyl-L-phenylalanyl-L-valine.

25. The method of claim 24 wherein said composition is admixed with a pharmaceutical acceptable vehicle prior to administration.

26. The method of claim 24 wherein said composition is injected intradermally.

27. The method of claim 24 wherein said composition is applied topically to the wound.

28. A method for enhancing the formation of a natural biologcial dressing composed primarily of serium proteins, comprising:
administering to a wound a therapeutcially effective amount of a composition comprising a derivative of GHL-Cu having the general formula:

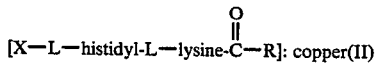

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

29. A method for enhancing the reestablishment of free, full-thickness skin flaps in warm-blooded animals, comprising:
administering to the skin flap an effective amount of a composition comprising a derivative of GHL-Cu having the general formula:

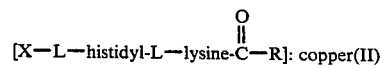

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

30. A method for enhancing the establishment of split-thickness skin grafts in warm-blooded animals, comprising:
administering to the skin graft an effective amount of a composition comprising a derivative of GHL-Cu having the general formula:

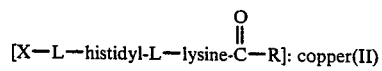

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

31. A method for increasing the rate of wound closure in warm-blooded animals, comprising:
administering to the animals an effective amount of a composition comprising a derivative of GHL-Cu having the general formula:

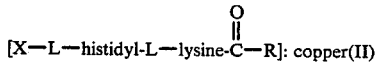

wherein X is glycyl-L-alanyl, glycyl-L-seryl, or glycyl-L-valyl, and wherein R is selected from the groups consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

* * * * *

UNITED STATES PATENT AND TRADEMARK OFFICE
CERTIFICATE OF CORRECTION

PATENT NO. : 4,810,693

DATED : March 7, 1989

INVENTOR(S) : Loren R. Pickart

It is certified that error appears in the above-identified patent and that said Letters Patent is hereby corrected as shown below:

On the cover page, under References Cited, please insert the following:

U.S. Patent Documents

| | | |
|---|---|---|
| 3,194,732 | 7/65 | Neuhauser |
| 3,551,554 | 12/70 | Herschler |
| 3,558,770 | 1/71 | Gordon et al. |
| 3,758,682 | 9/73 | Huber et al. |
| 3,767,784 | 10/73 | Gluck |
| 3,832,338 | 8/74 | Huber et al. |
| 4,022,888 | 5/77 | Huber et al. |
| 4,167,945 | 9/79 | Gottlieb |
| 4,177,261 | 12/79 | Dietze et al. |
| 4,263,428 | 4/81 | Apple et al. |
| 4,287,184 | 9/81 | Young |
| 4,440,788 | 4/84 | Terayama et al. |

UNITED STATES PATENT AND TRADEMARK OFFICE
CERTIFICATE OF CORRECTION

PATENT NO. : 4,810,693
DATED : March 7, 1989
INVENTOR(S) : Loren R. Pickart

It is certified that error appears in the above-identified patent and that said Letters Patent is hereby corrected as shown below:

On the cover page, under References Cited, please insert the following:

OTHER PUBLICATIONS

Pickart et al, "Growth-Modulating Tripeptide (glycylhistidyllysine): "Association with Copper and Iron in Culture by Tripeptide-Metal Ion Complexes," J. Cell Physiol., 102(2), pp. 129-139, 1980. (Cited in Chem. Abstracts, Vol. 93:1155m, 1980.

Williams et al., "Glycyl-L-Histidyl-L-Lysine, a Growth Promoting Factor for Human Cells," Cytobios, 27(105), pp.19-25, 1980. (Cited in Chem. Abstracts, Vol. 94:25451b., 1981).

Mochida Pharmeutical Co., Ltd., "Antiinflammatory Injections Containing Superoxide Dismutase," Jpn. Kokai Tokkyo Koho, 81 07,720, 27 January 1981 (cited in Chem. Abstracts, Vol. 94:145386f, 1981)

Kwa, "Glycyl-L-Histidyl-L-Lysine: Synthesis of Analogs and NMR Studies," Ph.D. Thesis, University of Washington, 1983.

UNITED STATES PATENT AND TRADEMARK OFFICE
CERTIFICATE OF CORRECTION

PATENT NO. : 4,810,693
DATED : March 7, 1989
INVENTOR(S) : Loren R. Pickart

It is certified that error appears in the above-identified patent and that said Letters Patent is hereby corrected as shown below:

On the cover page, under References Cited, please insert the following:

OTHER PUBLICATIONS

Natural Healing Annual 1986, p.38 (Edit M. Bricklin, Prevention Magazine, Rodale Press, Emmaus, PA).

Pickart et al., "A Synthetic Tripeptide which Increases Survival of Normal Liver Cells and Stimulates Growth in Hepatoma cells," Biochem. Biophys. Res. Commun., 54(2), pp. 526-6, 1973.

UNITED STATES PATENT AND TRADEMARK OFFICE
CERTIFICATE OF CORRECTION

PATENT NO. : 4,810,693

DATED : March 7, 1989

INVENTOR(S) : Loren R. Pickart

It is certified that error appears in the above-identified patent and that said Letters Patent is hereby corrected as shown below:

On the cover page, under References Cited, please insert the following:

OTHER PUBLICATIONS

Loker, "Synthesis of Blood Serum Peptide Cell Growth Factors," Ph.D. Thesis, University of Washington 1980.

Pickart, "The Biological Effects and Mechanism of Action of the Plasma Tripeptide Glycyl-L-Histidyl-L-Lysine," Lymphonkines, 8, pp. 425-446, 1983.

Poole et al., "Stimulation of Rat Peritoneal Mast Cell Migration by Tumor-Derived Peptides," Cancer Research, 43, pp. 5857-5861, 1983.

Raju et al., "Ceruloplasmin, Copper Ions, and Angiogenesis," JNCI, 69(5), PP. 1183-1188, 1982.

UNITED STATES PATENT AND TRADEMARK OFFICE
CERTIFICATE OF CORRECTION

PATENT NO. : 4,810,693
DATED : March 7, 1989
INVENTOR(S) : Loren R. Pickart

It is certified that error appears in the above-identified patent and that said Letters Patent is hereby corrected as shown below:

On the cover page, under References Cited, please insert the following:

OTHER PUBLICATIONS

Sorenson, "Copper Complexes: A Physiologic Approach to Treatment of Chronic Diseases," Comprehensive Therapy, 11(4), pp. 49-64, 1985.

Pickart et al., "Inhibition of the Growth of Cultured Cells and an Implanted Fibrosarcoma by Aroylhydrazone Analogs of the Gly-His Lys-Cu(II) Complex," Biochem. Pharmacol., 32(24), pp. 3868-3871, 1983.

Pickart et al., "Growth-Modualating Plasma Tripeptide May Function By Facilitating Copper Uptake Into Cells," Nature, 288, pp. 715-717, 1980.

UNITED STATES PATENT AND TRADEMARK OFFICE
CERTIFICATE OF CORRECTION

PATENT NO. : 4,810,693

DATED : March 7, 1989

INVENTOR(S) : Loren R. Pickart

It is certified that error appears in the above-identified patent and that said Letters Patent is hereby corrected as shown below:

On the cover page, under References Cited, please insert the following:

OTHER PUBLICATIONS

Freedman et al., "Stucture of the Glycyl-L-Histidyl-Lysine-Copper(II) Complex in Solution," Biochemistry, 21, pp. 4540-4544, 1982.

Kwa et al., "PMR Studies of Cu(II) and Zn(II) Interaction with Glycyl-L-Histidyl-L-Lysine and Related Peptides," Peptides: Structure and Function, 8, pp. 805-808, 1983.

Perkins et al., "The Structure of a Copper Complex of the Growth factor Glycyl-L-Histidyl-L-Lysine at 1.1 A Resolution," Inorganica Chimica Acta, 82, pp. 93-99, 1984.

Kimoto et al., "Enhancement of Antitumor Activity of Ascorbate Against Ehrlich Ascites Tumor Cells by the Copper: Glycylglycylhistidine Complex," Cancer Research, 43, pp. 824-828, 1983.

UNITED STATES PATENT AND TRADEMARK OFFICE
CERTIFICATE OF CORRECTION

PATENT NO. : 4,810,693
DATED : March 7, 1989
INVENTOR(S) : Loren R. Pickart

It is certified that error appears in the above-identified patent and that said Letters Patent is hereby corrected as shown below:

In claim 4, column 11, line 48, delete "to 12" and substitute therefor --to 18--.

In claim 8, column 12, line 5, delete "alkyl" and substitute therefor --alykoxy--, line 6, delete "aryl" and substitute therefor --aryloxy--.

In claim 10, column 12, line 13, delete "alkyl" and substitute therefor --carbon portion of the alkoxy--.

In claim 11, column 12, line 16, delete "N-octyl" and substitute therefor --n-octyl--.

In claim 12, column 12, lines 17-18, delete "alkyl moiety is an N-stearyl" and substitute therefor --carbon portion of the alkoxy moiety is an n-stearyl--.

In claim 13, column 12, line 19, delete "aryl" and substitute therefor --carbon portion of the aryloxy--.

UNITED STATES PATENT AND TRADEMARK OFFICE
CERTIFICATE OF CORRECTION

PATENT NO. : 4,810,693

DATED : March 7, 1989

INVENTOR(S) : Loren R. Pickart

It is certified that error appears in the above-identified patent and that said Letters Patent is hereby corrected as shown below:

In claim 17, column 12, line 46, delete "to 12 carbons" and substitute therefor --to 18 carbons--.

In claim 24, line 12, after "alkoxy" insert --moieties containing from 1 to 18 carbon atoms, and aryloxy--

In claim 28, column 13, line 41, delete "from 1 to 12" and substitute therefor --from 1 to 18--.

In claim 29, column 14, line 10, delete "from 1 to 12" and substitute therefor --from 1 to 18--.

In claim 30, column 14, line 29, delete "from 1 to 12" and substitute therefor --from 1 to 18--.

In claim 31, column 14, line 48, delete "from 1 to 12" and substitute therefor --from 1 to 18--.

Signed and Sealed this

Twenty-fifth Day of September, 1990

Attest:

HARRY F. MANBECK, JR.

*Attesting Officer*  *Commissioner of Patents and Trademarks*